United States Patent [19]

Becker et al.

[11] Patent Number: 4,931,343
[45] Date of Patent: Jun. 5, 1990

[54] SHEET MATERIAL USED TO FORM PORTIONS OF FASTENERS

[75] Inventors: Dennis L. Becker; Miroslav Tochacek; Paul E. Hansen, all of St. Paul, Minn.

[73] Assignee: Minnesota Mining and Manufacturing Company, Saint Paul, Minn.

[21] Appl. No.: 147,137

[22] Filed: Jan. 22, 1988

Related U.S. Application Data

[63] Continuation-in-part of Ser. No. 760,999, Jul. 31, 1985.

[51] Int. Cl.[5] .............................................. B32B 3/02
[52] U.S. Cl. ........................................ 428/95; 66/191; 66/192; 156/72; 428/85; 428/92; 428/93; 428/100; 428/296
[58] Field of Search .................. 66/190, 191, 194, 192; 428/85, 92, 93, 95, 99, 100, 296; 156/72

[56] References Cited

U.S. PATENT DOCUMENTS

| | | | |
|---|---|---|---|
| 3,009,235 | 11/1961 | Mestral | 28/78 |
| 3,527,629 | 9/1970 | Wylde | 156/72 |
| 3,701,700 | 10/1972 | Von Der Herde | 428/93 |
| 3,708,384 | 1/1973 | Carpenter | 428/93 |
| 3,708,837 | 1/1973 | Cheba | 24/204 |
| 4,216,257 | 8/1980 | Schams et al. | 428/93 |
| 4,290,832 | 9/1981 | Holleberg | 156/72 |
| 4,371,576 | 2/1983 | Machell | 428/93 |
| 4,454,183 | 6/1984 | Wollman | 428/92 |
| 4,463,486 | 8/1984 | Matsuda | 28/161 |
| 4,609,581 | 9/1986 | Ott | 428/100 |
| 4,673,604 | 6/1987 | Frain et al. | 428/95 |

FOREIGN PATENT DOCUMENTS

1091050 11/1967 United Kingdom .

*Primary Examiner*—James J. Bell
*Attorney, Agent, or Firm*—Donald M. Sell; Walter N. Kirn; William L. Huebsch

[57] ABSTRACT

A method for forming a sheet material adapted to be cut into smaller pieces to form portions of a fastener. The method comprises providing a self supporting polymeric film that provides the structural strength to retain the integrity of the sheet material, and stitching a plurality of yarns through the film to form loops projecting from one surface of the film and locking portions of the stitches adjacent the opposite surface of the film. The sheet material can also include a layer of heat softenable polymeric material adhered to the film over the locking portions.

32 Claims, 3 Drawing Sheets

SHEET MATERIAL USED TO FORM PORTIONS OF FASTENERS

CROSS REFERENCE TO RELATED APPLICATION

This invention is a Continuation in Part of U.S. Patent Application No. 760,999, filed July 31, 1985, and incorporated herein by reference.

TECHNICAL FIELD

The present invention relates to sheet materials that can be cut into smaller pieces to form portions of fasteners, and methods for forming such sheet materials.

BACKGROUND ART

The art is replete with various sheet materials that can be cut into smaller pieces to form portions of fasteners, and methods for making such sheet materials. U.S. Pat. No's. 3,009,235; 4,024,003; 4,290,832; 4,454,183 provide illustrative examples Generally these patents have described sheet materials including backings from which project yarns that form either loops, loops cut along one side to form hooks, or projections that have enlarged heads at their distal ends, and which backings anchor portions of the yarns so that the loops, hooks or headed projections on pieces of such material may be engaged with other such structures on pieces of other such sheet materials to form fasteners.

Such yarns have been either embedded into a polymeric backing layer while it was heat softened so that the yarns were fused to the backing; or woven into a cloth backing that was of regularly woven construction, which backing was then coated with an adhesive-like material applied by spraying, soaking or extruding so that the yarns were more solidly anchored in place. The former method provides extremely strong anchoring of the yarns by fusing them to the backing layer, however, it requires complex and expensive special equipment to make wide widths of the material. The latter method can be used to make materials in wide widths, however, it is slow and requires an extra step to apply the adhesive like material to the backing so that the cost of the resultant sheet material is relatively high.

DISCLOSURE OF THE INVENTION

The present invention provides a method for forming a sheet material of the type described above which is adapted to be cut into smaller pieces to form portions of a fastener, which method affords manufacturing the sheet material in wide widths on commercially available equipment with a backing formed primarily from inexpensive polymeric film.

The method according to the present invention for forming a sheet material adapted to be cut into smaller pieces to form portions of a fastener comprises the steps of (1) providing a self supporting polymeric film; and (2) stitching a plurality of yarns through the film to form loops projecting from a first surface of the film and form locking portions of the stitches adjacent a second opposite surface of the film.

In sheet material according to the present invention formed by that method the film provides the structural strength to retain the integrity of the sheet material at least until after smaller pieces are cut from the sheet material and adhered to a substrate, so that no fibrous layers, such as non woven, random woven, knitted or woven layers are required to form the sheet material. Such use of film in the backing of such sheet material can provide many advantages over the use of fibrous layers including more fray resistance and dimensional stability than non woven backings; flat non porous surfaces that can be adhered to a substrate with thinner coatings of the same adhesives than could adhere a fibrous layer to that substrate, or that can be printed on to form graphics which can be easily seen through the loops and can provide decoration or information about an object to which the fastener portion is attached, such as its size, instructions for its use, or a trademark; and transparent portions of the backing through which such printing can be seen so that the printing can be sealed and protected between layers of the backing; and is generally believed to provide the lowest cost substrate for providing a given level of anchoring and support for loops, hooks or headed projections in a mechanical fastener portion. The film used in the backing of such sheet material can also be adapted to provide desired properties for the sheet material. For example, film can be selected that is soft and non abrasive to the skin for use in a fastening element on a disposable diaper or bandage where skin contact is possible. The film can be of or include a foam polymeric material where a cushioned fastening element is desired, or the film can provide a carrier for scents, pigments, or other functional fillers.

Also, the method can include a variety of method steps for providing heat softenable polymeric material in the backing which can be adhered to the film over the locking portions of the stitches or have the stitches extend through it with the locking portions of the stitches along its surface opposite the film so that the heat softenable material may be adhered to the locking portions of the stitches to anchor the stitches, and if the yarns are of heat softenable polymeric material, the locking portions of the stitches may be fused together and to the layer of heat softenable polymeric material to even further anchor the stitches.

In addition to anchoring the yarns in the backing laminate, the polymeric material from the sealing layer can also provide means for heat sealing pieces of the sheet material to a substrate by heating the pieces so that the polymeric material from the sealing layer softens and adheres to the substrate.

The method as described above may be used to form sheet material having projecting loops either by using monofilament yarns to provide maximum loop strength for a given yarn diameter, or, preferably, by using multifilament yarns that, compared to monofilament yarns, can greatly increase the number of loops formed for a given number of stitches. Alternatively, sheet material having a plurality of projecting hooks may be made by using monofilament yarns of a heat settable polymer (e.g., nylon or polyester) and adding the further steps of heating the loops so that they will resiliently retain their shape, and cutting each loop along one side to form the hooks; or sheet material having projections with enlarged heads on their distal ends may be made by using monofilament yarns to form the loops and the further step of heating the upper portions of the loops to melt their central portions and form from each loop two projections with enlarged heads on their distal ends. Such heads can be made mushroom or globular shaped by selecting the proper polymeric material for the yarns (e.g., polypropylene or nylon respectively) as is well known in the art, or can be caused to have hook-like portions projecting from the heads along the yarns that connect them to the backing by using monofilament yarns of polypropylene with lobes around their peripheries as is taught in U.S. Pat. No. 4,454,183 incorporated herein by reference.

At present the only known machines capable of stitching the yarns through the base material or backing laminate at commercially acceptable rates are the Malimo — type Malipol Stitch-Knitting Machine manufactured by Textima in East Germany and distributed in the U.S. by Chima, Inc. of Reading, Pennsylvania; and the Czechloslovak version ARACHNE Stitch bonding machine type Araloop, sold in the U.S. by Omintex in Charlotte, North Carolina. It is believed, however, that new stitch knitting machines are presently under development by American Liba Corp. and Karl Mayer of West Germany that will also provide the needed stitching capability.

Such known stitch-knitting or stitch bonding machines are available that can apply the stitches to backings over 140 inches wide, can apply up to 1500 stitches per minute while applying about 12 stitches per inch (which is usable for forming sheet material according to the present invention), thereby producing stitched backing at a speed of about 625 feet per hour which is about 2 to 10 times greater than the speed at which similar looped structures could be produced by known weaving or knitting machines.

The loop height (i.e., the average height that the centers of the loops project above the base material) has been varied in the range of 1 to 5 millimeters on the stitch-knitting machine and loops having heights in that range have been found to make acceptable engagement with hooks or headed stems on mating sheet material, or have been found to produce acceptable hooks or headed stems when further processed in accordance with the methods described above.

Preferably the loops are formed by making 5.5 to 7 longitudinal rows of stitches or wales per centimeter (14 to 18 wales per inch) measured in a direction at a right angle to the wales, and making 3.9 to 10 stitches or courses per centimeter (10 to 25 courses per inch) along each row or wale. It has been found that increasing the stitch density not only increases the number of anchoring sites for the stitches, but also causes the loops that are formed to stand more erect.

The self supporting polymeric film should have sufficient thickness to firmly anchor the stitches and provide support for the loops so that they will project outwardly from the front face of the backing, should have high resistance to tearing despite the multiplicity of holes punched through the film by the needles used to form the stitches, and should have a low elongation ratio so that the needles forming the stitches can punch cleanly through the film without excessively stretching the portions of the film around the holes formed by the needles. Tests on films using ASTM D 1922-67 Standard Test Method for Propagation Tear Resistance of Plastic Film and Thin Sheeting by the Pendulum Method (a copy of which test procedure, incorporated herein by reference, is available from the American Society for Testing and Materials, 1916 Race Street, Philadelphia, PA 19103) using an Elmendorf Tear Tester, Model 60-16, available from the Thwing Albert Instrument Co., Philadelphia, PA, have shown that films that have a tear resistance of above 0.04 kilograms and preferably above 0.055 kilograms as measured by that test are suitable for use in the present invention.

Also, tests on films using ASTM D 882-80a Standard Test Method for Tensile Properties of Thin Plastic Sheeting (a copy of which test procedure, incorporated herein by reference, is also available from the American Society for Testing and Materials, 1916 Race Street, Philadelphia, PA 19103) using an Instron model 1122, have shown that films that require a tensile force of at least 0.035 kilograms per centimeter and preferably require a tensile force of greater than 0.75 kilograms per centimeter to elongate the films to 5% greater than their original length are suitable for use in the present invention. A preferred film that can adequately meet the requirements set out above is a high molecular weight high density polyethylene film at least about 0.0038 centimeter (0.0015 inch) thick up to about 0.0127 centimeter (0.005 inch), and preferably in the range of about 0.0044 to 0.0076 centimeter (0.00175 to 0.003 inch) thick, however other films such as polypropylene and copolymers and blends thereof have also been found useful.

The purpose of the sealing layer of heat softenable material is to provide material that, when heated will flow around and bond to the locking portions of the stitches to anchor the yarns to the film. Suitable heat softenable polymeric materials for use in the sealing layer include polyalkylenes such as polyethylene, polypropylene and the like, polyesters having an ester linkage in the backbone chain such as polyethylene terephthalate, polyamides such as nylons, polyvinyl chloride, polysulfones, polystyrene and polyurethanes such as polyether polyurethanes. Copolymers of the monomers which provide the above polymers are also useful. Presently preferred materials are polyethylene, polypropylene, the copolymers of ethylene and acrylic acid, the copolymers of ethylene and propylene and the copolymers of ethylene and vinyl acetate. Film layers of these preferred materials in the thickness range of about 0.0013 to 0.05 centimeter (0.0005 to 0.02 inch) and preferably in the range of about 0.005 to 0.013 centimeter (0.002 to 0.005 inch) have been found to be useful, with the thicker layers being preferable when pieces of the sheet material are to be heat fused to a substrate by those layers.

BRIEF DESCRIPTION OF THE DRAWING

The present invention will be further described with reference to the accompanying drawing wherein like numbers refer to like parts in the several views, and wherein.

DETAILED DESCRIPTION OF THE DRAWING

Figure 1:
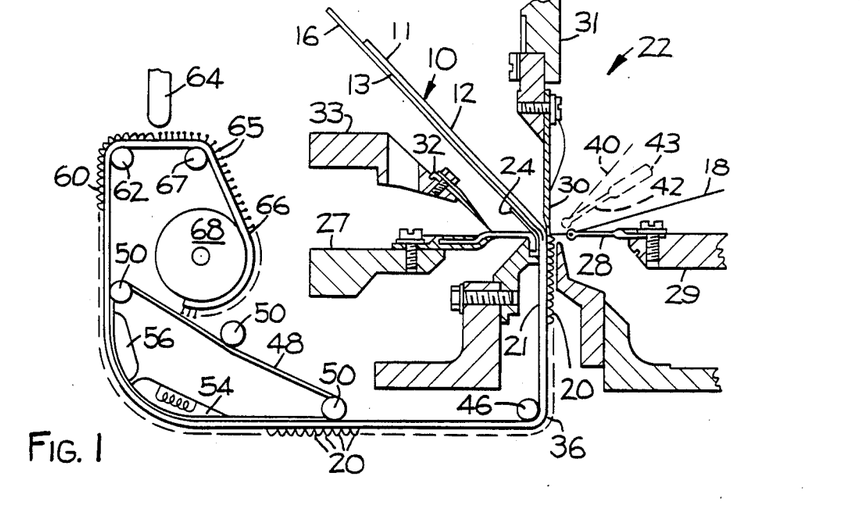
FIG. 1 schematically illustrates a method according to the present invention for making the sheet materials according to the present invention shown in FIGS. 2 through 11.

Referring now to FIG. 1 of the drawing, there is schematically illustrated a method according to the present invention for forming several sheet materials adapted to be cut into smaller pieces to form portions of a fastener.

Generally the method illustrated in FIG. 1 comprises the steps of providing a self supporting polymeric film 11 having first and second major surfaces 12 and 13 that is to be included in and provide the structural integrity for a backing 10 for the sheet material to be formed. A sealing layer 16 of heat softenable polymeric material is also provided in the backing 10 and is disposed along the second major surface 13 of the film 11 either by being coated on the film 11 (e.g., by extrusion coating), or by having a film of the heat softenable polymeric material positioned along the second surface 13 of the film 11, or by providing the film 11 and sealing layer 16 as a coextrusion. A plurality of yarns 18 are stitched through the entire backing 10 to form portions of the yarns 18 into loops 20 projecting from a front face of the backing 10 and locking portions 21 of the stitch adjacent the second surface 13 of the film 11 and along the outer surface of the sealing layer 16 of polymeric material. Such stitching is accomplished by a stitch-knitting or stitch bonding machine 22 (e.g., a Malimo~ type Malipol Stitch-knitting Machine). The stitch-knitting machine 22 can be used in various ways, but as used in this invention comprises means including a guide 24 for guiding the backing 10 from a downwardly sloping path portion to a vertical path portion, a row of horizontal evenly spaced parallel needles 26 fixed to a needle bar 27, which needles 26 have recesses spaced from their points, and are longitudinally reciprocated by the needle bar 27 to repeatedly pierce the backing 10 at the junction between the sloping and vertical path portions as the backing 10 is moved past that junction, a row of evenly spaced yarn guides 28 attached to a bar 29 positioned on the side of the path for the backing 10 opposite the needles 26, which yarn guides 28 have openings in their distal ends through which the yarns 18 are guided and can locate the yarns 18 to engage them with the recesses in the needles 26 when the ends of the needles 26 have pierced the backing 10, a row of vertically downwardly projecting loop sinkers 30 fixed to a support 31, around which loop sinkers 30 the loops 20 are formed, and a row of closing wires 32 fixed to a support 33, each of which wires 32 moves both with and relative to an associated needle 26 to cover and uncover the recess spaced from the point of that needle 26 at appropriate times in the operating cycle of the machine 22.

Generally, as used in the method according to the present invention, the stitch-knitting machine 22 is operated as a stitching machine so that repeatedly the row of horizontal needles 26 pierces the backing 10 while passing between the loop sinkers 30 so that the points and recesses along the needles 26 move between and past the loop sinkers 30 to an extended position between the yarn guides 28, while the closing wires 32 move relative to the needles 26 to open the recesses in the needles 26 when the needles 26 arrive in that extended position. Simultaneously, the bar 29 moves the yarn guides 28 in a generally semicircular pattern around the ends of the needles 26 to lay yarns 18 guided through openings in the yarn guides 28 into the open recesses in the needles 26. The needles then are pulled back through the backing 10 as the closing wires 32 again move relative to the needles 26 to close the recesses so that the needles 26 will pull the yarns 18 through the backing 10. The backing laminate is advanced between repetitions of this cycle at a rate that determines the lengths of the stitches that are formed by subsequent piercing of the backing 10 by the needles 26.

The machine 22 can be operated by using an appropriate cam in conjunction with the bar 29 so that in addition to moving the yarn guides 28 around the ends of the needles 26 to lay the yarns 18 in the recesses in the needles 26, the bar 29 will also move the yarn guides 28 back and forth between two adjacent needles 26 positioning each length of yarn 18 in one needle 26 the first time the needles pierce the backing 10 and in the other needle 26 the next time the needles pierce the backing 10. Thus the length of yarn 18 extends around the loop sinker 30 between those two adjacent needles 26 each time the yarn 18 is pulled through the backing 10 to form the loops 20. When operated in this single bar mode the machine 22 will form a stitched intermediate material 36a illustrated in FIGS. 2, 3 and 4 comprising the backing 10 consisting of the film 11 and sealing layer 16, and a plurality of rows of the yarn 18 stitched through the backing 10 and having portions forming the loops 20 projecting from the first surface 12 of the film 11 and the locking portions 21 locking the stitches adjacent the second surface 13 of the film 11 and along the sealing layer 16 of polymeric material.

Figure 5:
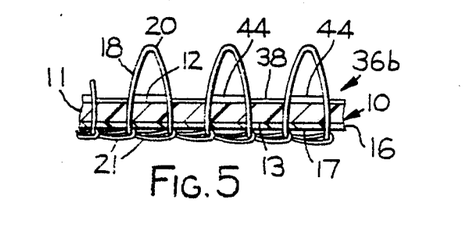
FIG. 5 is an enlarged sectional edge view of a second embodiment of a sheet material that can be made by the method shown in FIG. 1.
Figure 6:
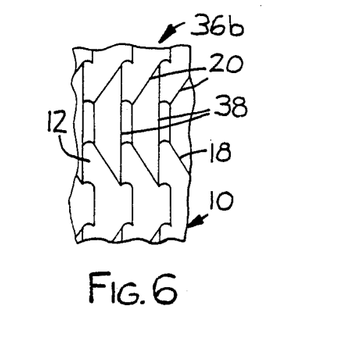
FIG. 6 is a fragmentary top view of the sheet material of FIG. 5.

Alternatively, the machine 22 can be operated by providing and using an appropriate cam in conjunction with the bar 29 so that in addition to moving the yarn guides 28 around the ends of the needles 26 to lay the yarn 18 in the recesses in the needles 26, the bar 29 will also move the yarn guides 28 between adjacent needles 26 after each second piercing of the backing 10, thereby positioning each length of yarn 18 in the same first needle 26 the first two times the needles 26 pierce the backing 10, and in an adjacent needle 26 the next two times the needles 26 pierce the backing 10 as a completion of the pattern repeat which starts again by the yarn guides 28 placing the yarn 18 in the first needle 26 the next two times the needles pierce the backing 10. Thus the length of yarn 18 extends around the loop sinker 30 between those adjacent needles 26 each second time the yarn 18 is pulled through the backing 10. Each needle also sews a second yarn 40 into the backing 10 by using a second set of yarn guides 42 attached to a bar 43 (shown in dotted outline in FIG. 1) to guide the yarns 40. A cam used in conjunction with the bar 43 continuously moves each of the second yarn guides 42 around the end of the same needle 26 to lay the second lengths of yarn 40 in the recesses in that needle 26 when it is in its extended position so that the second lengths of yarn 40 are never positioned around the loop sinkers 30 between two adjacent needles 26. When operated in this double bar mode the machine 22 will form a stitched intermediate material 36b illustrated in FIGS. 5 and 6 comprising the backing 10 consisting of the film 11 and sealing layer 16, a plurality of rows of the yarn 18 stitched through the backing 10 and having portions forming loops 20 projecting from the first surface 12 of the film 11, a reinforcing portion 38 along the first surface 12 of the film 11 between each loop 20 that adds longitudinal strength to the backing 10, and locking portions that are the same as the locking portions 21 shown in FIG. 4 locking the stitches adjacent the second surface 13 of the film 11 and along the sealing layer 16 of polymeric material, and a plurality of corresponding rows of the second yarns 40 stitched through the backing 10 and having reinforcing portions 44 at the base of each loop 20 laying along the first surface 12 of the film 11, and locking portions 21 locking the stitches adjacent the second surface 13 of the film 11 and along the outer surface of the sealing layer 16 of polymeric material.

Figure 2:
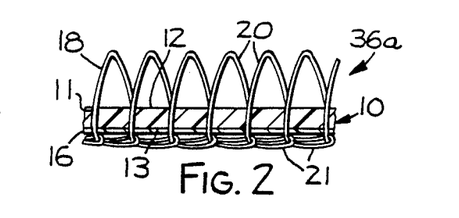
FIG. 2 is an enlarged sectional edge view of a first sheet material that can be made using a portion of the method shown in FIG. 1.
Figure 3:
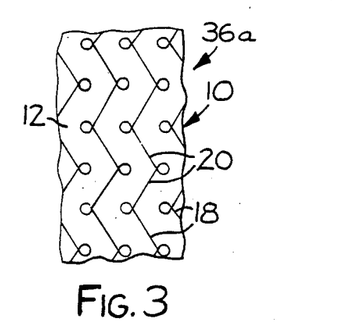
FIG. 3 is a fragmentary top view of the sheet material of FIG. 2.
Figure 4:
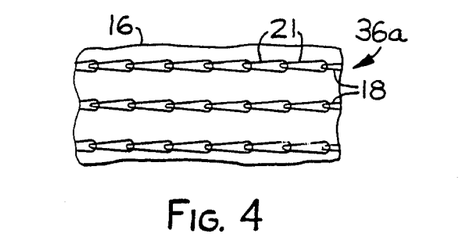
FIG. 4 is a fragmentary bottom view of the sheet material of FIG. 2.
Figure 7:
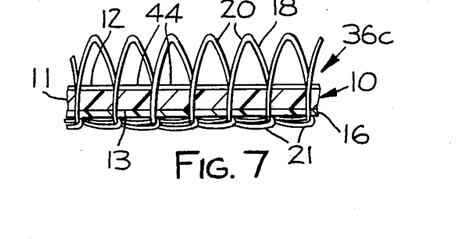
FIG. 7 is an enlarged sectional edge view of a third embodiment of a sheet material that can be made using a portion of the method shown in FIG. 1.
Figure 8:
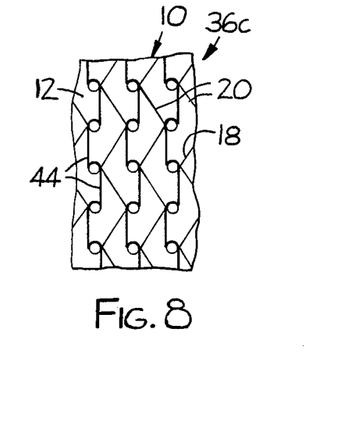
FIG. 8 is a fragmentary top view of the sheet material of FIG. 7.

Also, the machine 22 can be operated in the manner described above to make the intermediate material 36a illustrated in FIGS. 2, 3 and 4, and modified so that each needle also sews a second yarn 40 into 10 by using a second set of yarn guides 42 attached to a bar 43 (shown in dotted outline in FIG. 1) to guide the yarns 40. A cam used in conjunction with the bar 43 continuously moves each of the second yarn guides 42 around the end of the same needle 26 to lay the second lengths of yarn 40 in the recesses in that needle 26 when it is in its extended position so that the second lengths of yarn 40 are never positioned around the loop sinkers 30 between two adjacent needles 26. When operated in this double bar mode the machine 22 will form a stitched intermediate material 36c illustrated in FIGS. 7 and 8 comprising the backing 10 including the film 11 and the sealing layer 16, a plurality of rows of the yarn 18 stitched through the backing 10 and having portions forming the loops 20 projecting from the first surface 12 of the film 11 and locking portions 21 locking the stitches adjacent the second surface 13 of the film 11 and along the outer surface of the sealing layer 16 of heat softenable polymeric material, and a plurality of corresponding rows of the second yarns 40 stitched through the backing 10 and having tightening portions 44 at the base of each loop 20 laying along the first surface 12 of the film 11, and locking portions 21 locking the stitches adjacent the second surface 13 of the film 11 and along the outer surface of the sealing layer 16 of heat softenable polymeric material.

Figure 9:
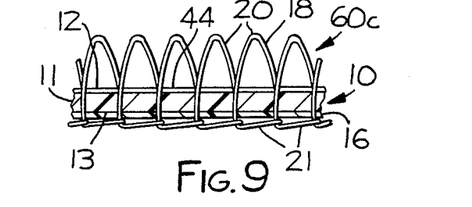
FIG. 9 is an enlarged sectional edge view of a fourth sheet material that can be made using a portion of the method shown in FIG. 1.

Subsequent to the loops 20 being formed by the machine 22, the stitched intermediate 36 (a, b or c) moves around a take-off roller 46 (FIG. 1) and then onto the surface of an endless metal belt 48 extending around three guide rollers 50, and along a heated shoe 54 and a cooling shoe 56, which belt 48 is driven in synchronism with the stitched intermediate 36 by a drive mechanism (not shown). As it passes over the heated shoe 54 and the cooling shoe 56, the belt 48 is first heated to a surface temperature (e.g., 245" C.) sufficient to soften the layer of polymeric material 16 and adhere it to the film 11 and the locking portions 21 of the stitches, and is then cooled to allow the polymeric material of the sealing layer 16 to separate from the belt 48. If the yarns 18 (and 40 if present) are of a heat softenable polymeric material, such heating by the shoe 54 through the belt 48 heats the locking portions 21 of the stitches to fuse them both to each other and to the softened polymeric material from the sealing layer 16 as is illustrated in FIG. 9.

Thus in the method illustrated in FIG. 1, the stitching and heating steps are performed continuously during movement of the backing 10 along the same production line through the stitch-knitting machine 22 and around the heated belt 48 to form sheet materials 60a, 60b, or 60c corresponding to the stitched intermediates 36a, 36b and 36c respectively (of which only sheet material 60c is shown, see FIG. 9), which sheet materials 60 (a, b or c) have projecting loops 20 and are adapted to be cut into smaller pieces to form portions of fasteners.

Sheet materials 60 having projecting loops 20 that are adapted to mate with sheet materials having projecting headed stems or hooks are preferably made using multifilament yarns 18 (and 40 if present) of between 70 and 300 denier and having between 26 and 36 filaments, and are preferably made in the form of sheet materials 60a and 60b.

Figure 10:
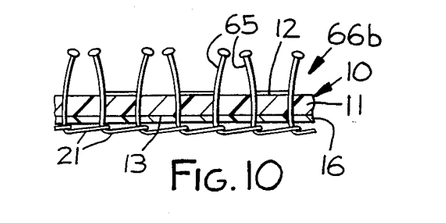
FIG. 10 is an enlarged sectional edge view of a fifth sheet material that can be made using the method shown in FIG. 1.

As an alternative to using the sheet material 60 (a, b, or c) in the form that it leaves the belt 48, when monofilament yarns 18 (e.g., 250 to 400 denier) are used to form the loops 20 (but not the yarns 40 which, if present, are still preferably multifilament yarns), the sheet material 60 (a, b or c) can be passed around an idle roller 62 and further processed on the same production line illustrated in FIG. 1 by passing the loops 20 under a heat source illustrated as a heated wire 64, but which could be other forms of heaters. The heated wire 64 causes the centers of the loops 20 to melt and form from each loop 20 two headed stems 65 as is illustrated in FIG. 10 which shows sheet material 66b produced from the stitched intermediate 36b, which is the preferred sheet material for forming headed stems 65 because of a lower tendency for adjacent headed stems 65 to fuse together as they are formed. Similar sheet materials 66a and 66c (not shown) could be made from the sheet materials 36a and 36c, however, if monofilament yarns are used to form their loops 20.

Figure 11:
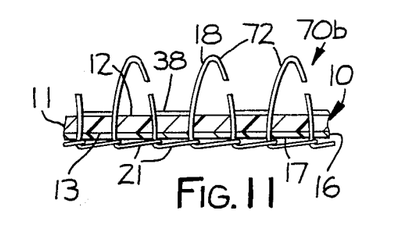
FIG. 11 is an enlarged sectional edge view of a sheet material having projecting hooks that can be made by a portion of the method shown in FIG. 1 and further processing illustrated in FIG. 12.
Figure 12:
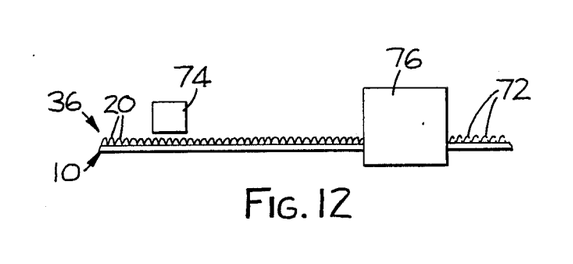
FIG. 12 schematically illustrates a method for further processing the sheet material of FIG. 11.

From the hot wire 64 the completed sheet material 66 (a, b or c) can be passed around a guide roller 67 and wound into a supply roll 68 from which smaller pieces may be cut to provide parts of fasteners. As an alternative to making the sheet materials 36 (a, b or c) with their projecting loops 20, or making sheet materials 66 (a, b or c) with headed stems 65 as described above, when monofilament yarns 18 are used to form the loops 20 (but not the yarns 40 which, if present, are still preferably multifilament yarns), the method may also be used to form sheet materials 70 (a, b or c) with projecting hooks 72 as illustrated by sheet material 70b in FIG. 11 by further processing the sheet material 36 (a, b or c) as is shown in FIG. 12. As illustrated in FIG. 12, the loops 20 of an appropriate yarn (e.g., nylon or polyester monofilament) may be heat treated as by a heat source 74 to cause them to resiliently retain their loop like shape, and may then be passed through a hook cutting device 76 (e.g., Loop Cutting Machine, Type PSM, made by Jacob Muller, Frick, Switzerland) to cut each loop along one side and form the hooks 72 on the sheet material 70 (a, b or c).

Figure 13:
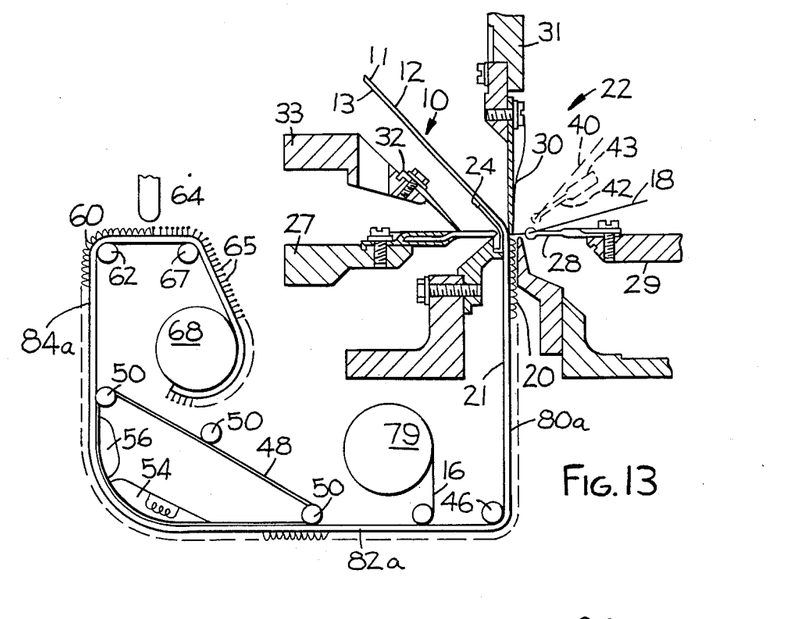
FIG. 13 schematically illustrates an alternative method according to the present invention for making stitched intermediate materials and sheet materials according to the present invention similar to those shown in FIGS. 2 through 11.
Figure 15:
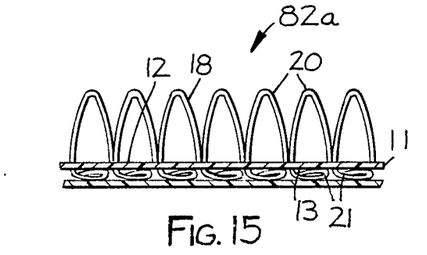
FIG. 15 is an enlarged sectional edge view of a stitched intermediate material that results during a portion of the method shown in FIG. 13.
Figure 16:
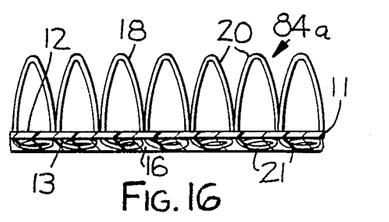
FIG. 16 is an enlarged sectional edge view of an eighth sheet material that can be made using the method shown in FIG. 13.

FIG. 13 illustrates an alternate method according to the present invention for forming several sheet materials adapted to be cut into smaller pieces to form portions of fasteners using the stitch-knitting machine 22 with the guide 24 for guiding the backing 10, the needles 26, the yarn guides 28 attached to the bar 29 (and the yarn guides 42 attached to the bar 43 if needed), the loop sinkers 30, and the closing wires 32, which machine 22 may be operated in any of the single and double bar modes described above to form the various patterns of loops and stitches; the endless metal belt 48, and the rollers 50, heated shoe 54 and cooling shoe 56 around which it extends; and the heated wire 64 (if needed). In the method illustrated in FIG. 13, unlike that illustrated in FIG. 1, however, only the self supporting polymeric film 11 is passed through the machine 22 so that the yarns 18 are only stitched through the film 11. When the machine 22 is thus operated in the single bar mode described above with reference to making the intermediate material 36a illustrated in FIGS. 2, 3, and 4 it will form the stitched film structure 80a illustrated in FIG. 14. The sealing layer 16 of heat softenable polymeric material is then fed in the form of a film from a supply roll 79 along the second surface 13 of the film 11 with the sealing layer 16 over the locking portions 21 of the stitches to form an intermediate material 82a illustrated in FIG. 15. When the intermediate material 82a is further processed by being passed over the heated and cooled belt 48, the resultant sheet material 84a (FIG. 16) produced will be very similar to the sheet material 60a produced by the method illustrated in FIG. 1 in that the layer of polymeric material 16 is adhered to the backing 10 and to the locking portions 21 of the stitches, and if the yarns 18 are of a heat softenable polymeric material, the locking portions 21 of the stitches may be fused both to each other to the softened polymeric material from the sealing layer 16. Alternatively, the stitched film structure 80a shown in FIG. 14 can removed from the machine 22 and heat softenable polymeric material can be applied to the second surface 13 of the film 11 over the locking portions 21 of the stitches by a method such as extrusion coating either prior to or as the stitched film structure 80a is applied to a substrate.

The method according to the present invention can further include printing on the first surface 12 or the second surface 13 of the film 11 to form graphics which can be easily seen through the loops and can provide decoration or information about an object to which a fastener portion cut from the sheet material is attached, such as its size, instructions for its use, or a trademark. Preferably, the printing is on the second surface 13 of the film 11, and the film is transparent so that the printing can be seen through the film 11. This both protects the printing from abrasion, and causes it to be sealed in the backing when the sealing layer 16 of heat softenable polymeric material is applied to prevent the ink used in the printing from rubbing off as a contaminant.

The method can also provide other decorative affects in the sheet material by using different colored yarns 18 so that stripes of different color are provided on the sheet material. A pronounced zigzag pattern can also be produced by using different colored yarns 18 and operating the machine in an "ATLAS" stitch style (not shown) which is somewhat like the single bar mode described above except that by using a different cam in conjunction with the bar 29, the bar 29, in addition to moving the yarn guides 28 around the ends of the needles 26 to lay the yarns 18 in the recesses in the needles 26, will also move each Yarn guide 28 in one direction from one adjacent needle 26 to the next and around an intervening loop sinker 30 between each two times the needles 26 pierce the backing 10 for five successive times the needles 26 pierce the backing 10, and will then move each yarn guide 28 in the other direction in the same way the next four times the needles 26 pierce the backing 10 to complete the pattern.

Film Property Test

To help determine the physical properties required for a film 11 that is suitable for use in making sheet material according to the present invention, several films were stitched with yarns as is described in Examples 1 through 4 below, and were also tested in both the machine direction and cross machine direction of the films for resistance to tear propagation in accordance with ASTM D1922 as described above, and for the tensile force required to elongate the films to 5% greater than their original length in accordance with ASTM D882, also described above. The resulting test the values are reported in Table 1. The films of Examples 1 to 4 which were found suitable for use as the backing for sheet material according to the present invention had minimum tear resistances of greater than about 0.04 kilogram and required a tensile force of greater than about 0.35 kilogram per centimeter to elongate to 5 percent greater than their original length. In contrast, the film of Example 2, which exhibited unacceptable tear resistance during processing on the machine 22 had a measured tear resistance of only 0.028 kilogram in the machine direction; and the film of Example 3, which stretched and distorted unacceptably during processing on the machine had a low measured tensile force of 0.29 kilogram per centimeter required to elongate the film by 5 percent.

TABLE 1

| FILM | TEST DIRECTION | TEAR RESISTANCE kg | TENSILE AT 5% ELONGATION kg/cm |
|---|---|---|---|
| EXAMPLE 1 | MD | 0.079 | 0.937 |
| | CD | 0.400 | 0.953 |
| EXAMPLE 2 | MD | 0.029 | 0.497 |
| | CD | 0.137 | 0.563 |
| EXAMPLE 3 | MD | 0.264 | 0.273 |
| | CD | 0.587 | 0.280 |
| EXAMPLE 4 | MD | 0.062 | 0.850 |
| | CD | 0.100 | 0.843 |

EXAMPLE 1

Figure 14:
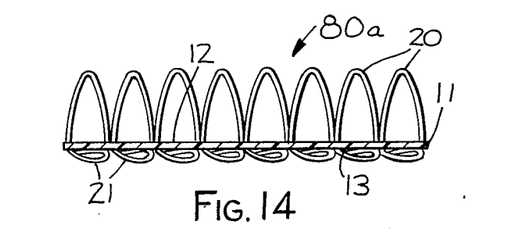
FIG. 14 is an enlarged sectional edge view of a seventh sheet material that can be made using a portion of the method shown in FIG. 13.

The stitched film structure 80a shown in FIG. 14 was prepared by stitching through a 45 micron (0.00175 inch) thick high molecular weight high density polyethylene film 11, commercially available as HMHDPE film from W.B.C. Extrusion Products Inc., Lowell, Massachusetts using a Malimo (TM) 14012 stitch-knitting machine 22 set to produce 3.94 courses or rows of stitches per centimeter (10 rows of stitches per inch) of width in the cross direction (i.e., the transverse direction with respect to the direction the film moves through the machine 22) and 5.51 wales or stitches per centimeter (14 stitches per inch) along each row of stitches in the machine direction (i.e. the direction the film moves through the machine 22), the loops 20 being formed by stitching 70 denier 34 strand multifilament texturized polyester yarn commercially available from Unifi Inc., Greensboro, North Carolina, over 4 mm loop sinkers 30, with 14 gauge or 0.56 millimeter diameter needles 26 to produce a stitched film having an overall basis weight of 60 grams per square meter. The film processed acceptably, did not stretch excessively around the holes formed by the needles 26 and did not shatter or tear during or after the stitching process, resulting in a stable stitched film from which loop fastener portions for a hook and loop fastener could be made.

EXAMPLE 2

The stitched film shown in FIG. 14 was prepared by stitching through a 25 micron (0.001 inch) thick high molecular weight high density polyethylene film 11, commercially available as HMHDPE film from W.B.C. Extrusion Products Inc., Lowell, Massachusetts using the same Malimo (TM) stitch-knitting machine 22 with the same needles 26, loop sinkers 30, and yarn 18, and with the machine 22 set to produce the same stitching pattern as in Example 1 to produce a stitched film having an overall basis weight of 42 grams per square meter. The film tore easily along the rows of stitches (in the machine direction) during the stitching process and thereafter due to propagation of tears from the holes made by the needles 26, and the film backing 11 of the resulting stitched film had little structural integrity and was judged unacceptable for use as sheet material according to the present invention.

EXAMPLE 3

The stitched film shown in FIG. 14 was prepared by stitching through a 51 micron (0.002 inch) thick ethylene vinyl acetate copolymer/linear low density polyethylene film that is commercially available as VA-24 film from Consolidated Thermoplastics, Chippewa Falls, Wisconsin using the same Malimo (TM) stitch-knitting machine 22 with the same needles 26, loop sinkers 30, and yarn 18, and with the machine 22 set to produce the same stitching pattern as in Example 1 to produce a stitched film having an overall basis weight of 66 grams per square meter. The film 11 stretched and distorted during the stitching process, which resulted in stitched film having poor uniformity which was judged unacceptable for use as sheet material according to the present invention.

EXAMPLE 4

The stitched film shown in FIG. 14 was prepared by stitching through a 63 micron (0.0025 inch) thick cast polypropylene film that was produced from a polypropylene resin having a melt flow index of 35 commercially available as PP-3085 from Exxon Chemical Corp., Houston, Tex., using same Malimo (TM) stitch-knitting machine 22 with the same needles 26, loop sinkers 30, and yarn 18, and with the machine 22 set to produce the same stitching pattern as in Example 1 to produce a stitched film having an overall basis weight of 78 grams per square meter. The film processed acceptably, did not stretch excessively around the holes formed by the needles 26 and did not shatter or tear during or after the stitching process, resulting in a stable stitched film from which loop fastener portions for a hook and loop fastener could be made.

Applications of the Present Invention

The stitched film shown in FIG. 14 was made as described in Example 1, and had a sealing layer 16 of 0.002 inch ethylene vinyl acetate film heat laminated over the locking portions 21 of the stitches to fuse the sealing layer 16 to the locking portions 21 and adhere it to the second surface 13 of the film 11. A piece cut from the resulting sheet material was then adhered the thin polyolefin film and nonwoven layers of a disposable diaper with a bonding layer of room-temperature nontacky thermoplastic material that was bonded to the polyolefin layer under heat and pressure that left the polyolefin layer substantially undeformed as is described in U.S. Patent Application No. 126,746 filed Nov. 30, 1987, the content whereof is incorporated herein by reference.

The stitched film shown in FIG. 14 was made as described in Example 1 except that the machine 22 was set to produce slightly more wales or stitches per centimeter along each row of stitches in the machine direction. The stitched film was then adhered by an extruded hot melt adhesive to the backing of a coated abrasive material as described in U.S. Pat. No. 4,609,581, the content whereof is incorporated herein by reference, to both seal the locking portions 21 of the stitches to the film 11 and adhere the stitched film to the coated abrasive material to provide means by which the coated abrasive material could be driven.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

We claim:

1. A method for forming a sheet material adapted to be cut into smaller pieces to form portions of a fastener, said method comprising the steps of:
   providing a self supporting polymeric film having first and second major surfaces; and
   stitching a plurality of yarns through only the film to form loops projecting from the first surface of the film and form locking portions of the stitches adjacent the second surface of the film.

2. A method according to claim 1 wherein said method further includes the steps of:
   positioning a film of heat softenable polymeric material along the second surface of the self supporting polymeric film and the locking portions of the stitches after said stitching step; and heating the film of heat softenable polymeric material to adhere it to the second surface of the self supporting polymeric film and the locking portions of the stitches.

3. A method according to claim 2 wherein the yarns are of a heat softenable polymeric material and said heating step includes heating the locking portions of the stitches to fuse them together and to the heat softenable polymeric material.

4. A method according to claim 2 wherein said stitching, positioning and heating steps are performed continuously during movement of the film along the same production line.

5. A method according to claim 1 wherein said method further includes the steps of:
   extruding a layer of heat softenable polymeric material along the second surface of the self supporting polymeric film and the locking portions of the stitches after said stitching step to adhere the heat softenable polymeric material to the second surface of the self supporting polymeric film and the locking portions of the stitches.

6. A method according to claim 5 wherein the yarns are of a heat softenable polymeric material and said extruding step heats the locking portions of the stitches to fuse them together and to the heat softenable polymeric material.

7. A method for forming a sheet material adapted to be cut into smaller pieces to form portions of a fastener, said method comprising the steps of:
   providing a self supporting polymeric film having first and second major surfaces;
   stitching a plurality of yarns through the film to form loops projecting from the first surface of the film and form locking portions of the stitches adjacent the second surface of the film; and
   printing graphics on one of the surfaces of the film prior to said stitching step.

8. A method for forming a sheet material adapted to be cut into smaller pieces to form portions of a fastener, said method comprising the steps of:
   providing a self supporting polymeric film having first and second major surfaces;
   stitching a plurality of yarns through the film to form loops projecting from the first surface of the film and form locking portions of the stitches adjacent the second surface of the film; and
   heating the upper portions of the loops to form from each loop two projections with enlarged heads on their distal ends.

9. A method for forming a sheet material adapted to be cut into smaller pieces to form portions of a fastener, said method comprising the steps of:
   providing a self supporting polymeric film having first and second major surfaces;
   stitching a plurality of yarns through the film to form loops projecting from the first surface of the film and form locking portions of the stitches adjacent the second surface of the film;
   heating the loops to cause them to resiliently retain their shapes; and
   cutting the loops along one side to form hooks.

10. A method for forming a sheet material adapted to be cut into smaller pieces to form portions of a fastener, said method comprising the steps of:
    providing a self supporting polymeric film having first and second major surfaces;
    adhering a layer of heat softenable polymeric material along the second surface of the self supporting polymeric film; and
    stitching a plurality of yarns through both the film and the layer of heat softenable polymeric material adhered to the film to form loops projecting from the first surface of the film and form locking portions of the stitches adjacent the second surface of the film along the layer of heat softenable polymeric material.

11. A method according to claim 10 wherein:
    the yarns are of a heat softenable polymeric material; and
    said method further includes the step of heating the locking portions of the stitches and the heat softenable polymeric material to fuse the locking portions of the stitches together and to the heat softenable polymeric material.

12. A method according to claim 11 wherein said stitching and heating steps are performed continuously during movement of the film along the same production film.

13. A method for forming a sheet material adapted to be cut into smaller pieces to form portions of a fastener, said method comprising the steps of:
    providing a self supporting polymeric film having first and second major surfaces;
    positioning a film of heat softenable polymeric material along the second surface of the self supporting polymeric film;
    stitching a plurality of yarns through both of the films to form loops projecting from the first surface of the film and form locking portions of the stitches adjacent the second surface of the film; and
    heating the film of heat softenable polymeric material to adhere the film of heat softenable polymeric material to the second surface of the film.

14. A method according to claim 13 wherein:
    the yarns are of a heat softenable polymeric material; and
    said step of heating the film of heat softenable polymeric material heats the locking portions of the stitches to fuse the locking portions of the stitches together and to the heat softenable polymeric material.

15. A method according to claim 13 wherein said stitching and heating steps are performed continuously during movement of the film along the same production line.

16. A method according to claim 1 wherein said film comprises two layers including a layer of heat softenable polymeric material defining the second surface of the self supporting polymeric film.

17. A method according to claim 16 wherein:
    the yarns are of a heat softenable polymeric material; and
    said method further includes the step of heating the locking portions of the stitches and the heat softenable polymeric material to fuse the locking portions of the stitches together and to the heat softenable polymeric material.

18. A method according to claim 17 wherein said stitching and heating steps are performed continuously during movement of the film along the same production line.

19. A sheet material adapted to be cut into smaller pieces to form portions of fasteners, which sheet material is made by the method of claim 1.

20. A sheet material adapted to be cut into smaller pieces to form portions of a fastener, said sheet material comprising:
    a backing having a front face and a back face, and comprising a self supporting polymeric film; and
    a plurality of yarns stitched through only said film having projecting portions projecting from the front face of said backing, and having locking portions on the side of said film opposite said projection portions;

said film providing the structural strength to retain the integrity of the sheet material.

21. A sheet material according to claim 20 wherein said locking portions are in contact with the side of said film opposite said projecting portions, and said backing includes a layer of heat softenable polymeric material defining the back face of the backing and adhered to said film over said locking portions.

22. A sheet material according to claim 21 wherein said yarns are of heat softenable polymeric material, and said locking portions of said stitches are fused together and to the layer of heat softenable polymeric material.

23. A sheet material adapted to be cut into smaller pieces to form portions of a fastener, said sheet material comprising:
   a backing having a front face and a back face, and comprising a self supporting polymeric film and a layer of heat softenable polymeric material defining the back face of the backing and adhered to said film; and
   a plurality of yarns stitched through both said film and said layer, said yarns having projecting portions projecting from the front face of said backing and having locking portions on the side of said film opposite said projecting portions along said back face;
   said film providing the structural strength to retain the integrity of the sheet material.

24. A sheet material according to claim 23 wherein said yarns are of heat softenable polymeric material, and said locking portions of said stitches are fused together and to said layer of heat softenable polymeric material.

25. A sheet material according to claim 20 wherein said film comprises two layers including a layer of heat softenable polymeric material defining the back face of the backing, and said locking portions are along said back face.

26. A sheet material according to claim 23 wherein said yarns are of heat softenable polymeric material, and said locking portions of said stitches are fused together and to said layer of heat softenable polymeric material.

27. A sheet material adapted to be cut into smaller pieces to form portions of a fastener, said sheet material comprising:
   a backing having a front face and a back face, and comprising a self supporting polymeric film having a low elongation ratio and high tear resistance; and
   a plurality of yarns stitched through said film having projecting portions projecting from the front face and said backing, and having locking portions on the side of said film opposite said projecting portions;
   said film providing the structural strength to retain the integrity of the sheet material.

28. A sheet material adapted to be cut into smaller pieces to form portions of a fastener, said sheet material comprising:
   a backing having a front face and a back face, and comprising a self supporting polymeric film of high molecular weight high density polyethylene at least 0.0015 inch thick; and
   a plurality of yarns stitched through said film having projecting portions projecting from the front face of said backing, and having locking portions on the side of said film opposite said projecting portions;
   said film providing the structural strength to retain the integrity of the sheet material.

29. A sheet material adapted to be cut into smaller pieces to form portions of a fastener, said sheet material comprising:
   a backing having a front face and a back face, and comprising a self supporting polymeric film, said film having opposite major surfaces and having printing along one of said surfaces; and
   a plurality of yarns stitched through said film having projecting portions projecting from the front face of said backing, and having locking portions on the side of said film opposite said projecting portions;
   said film providing the structural strength to retain the integrity of the sheet material.

30. A sheet material adapted to be cut into smaller pieces to form portions of a fastener, said sheet material comprising:
   a backing having a front face and a back face, and comprising a self supporting polymeric film; and
   a plurality of yarns stitched through said film having projecting portions projecting from the front face of said backing and forming loops, and having locking portions on the side of said film opposite said projecting portions;
   said film providing the structural strength to retain the integrity of the sheet material.

31. A sheet material adapted to be cut into smaller pieces to form portions of a fastener, said sheet material comprising:
   a backing having a front face and a back face, and comprising a self supporting polymeric film; and
   a plurality of yarns stitched through said film having projecting portions projecting from the front face of said backing, and having locking portions on the side of said film opposite said projecting portions, with some of said projecting portions of said yarns being resiliently flexible hooks;
   said film providing the structural strength to retain the integrity of the sheet material.

32. A sheet material adapted to be cut into smaller pieces to form portions of a fastener, said sheet material comprising:
   a backing having a front face and a back face, and comprising a self supporting polymeric film; and
   a plurality of yarns stitched through said film having projecting portions projecting from the front face of said backing, and having locking portions on the side of said film opposite said projecting portions, said projecting portions of said yarns having enlarged heads at their distal ends;
   said film providing the structural strength to retain the integrity of the sheet material.

* * * * *